(12) United States Patent
David et al.

(10) Patent No.: US 8,165,270 B2
(45) Date of Patent: Apr. 24, 2012

(54) X-RAY OPTICAL GRATING AND METHOD FOR THE PRODUCTION THEREOF, AND X-RAY DETECTOR EMBODYING SAME

(75) Inventors: Christian David, Lauchringen (DE); Tilman Donath, Brugg (CH); Eckhard Hempel, Fuerth (DE); Martin Hoheisel, Erlangen (DE); Barbara Matthis, Stutensee (DE); Franz Pfeiffer, Brugg (CH); Stefan Popescu, Erlangen (DE)

(73) Assignees: Paul Scherrer Institut, PSI (CH); Siemens Aktiengesellschaft, Munich (DE)

( * ) Notice: Subject to any disclaimer, the term of this patent is extended or adjusted under 35 U.S.C. 154(b) by 397 days.

(21) Appl. No.: 12/566,858

(22) Filed: Sep. 25, 2009

(65) Prior Publication Data
US 2010/0246769 A1    Sep. 30, 2010

(30) Foreign Application Priority Data
Sep. 26, 2008  (DE) .......................... 10 2008 049 200

(51) Int. Cl.
*G21K 1/00* (2006.01)
(52) U.S. Cl. ...................................................... 378/145
(58) Field of Classification Search ................... 378/145
See application file for complete search history.

(56) References Cited

U.S. PATENT DOCUMENTS

| | | | |
|---|---|---|---|
| 6,951,628 B2 * | 10/2005 | Eidam et al. ................... | 378/145 |
| 2007/0183562 A1 | 8/2007 | Popescu et al. | |
| 2007/0183563 A1 | 8/2007 | Baumann et al. | |
| 2007/0183579 A1 | 8/2007 | Baumann et al. | |
| 2007/0183582 A1 | 8/2007 | Baumann et al. | |
| 2007/0183583 A1 | 8/2007 | Baumann et al. | |
| 2007/0183584 A1 | 8/2007 | Baumann et al. | |
| 2007/0189449 A1 | 8/2007 | Baumann et al. | |
| 2009/0154640 A1 | 6/2009 | Baumann et al. | |

OTHER PUBLICATIONS

"Phase Tomography by X-ray Talbot Interferometer," Momose et al, SRI (2006).
"Moduliga: The LIGA Process as a Modular Production Method-Current Standardization Status in Germany," Hahn et al., Microsystem Technologies, vol. 11 (2005) pp. 240-245.

* cited by examiner

Primary Examiner — Glen Kao
(74) Attorney, Agent, or Firm — Schiff Hardin LLP

(57) ABSTRACT

In a method for the production of x-ray-optical gratings composed of a first material forming of periodically arranged grating webs and grating openings, a second material is applied by electroplating to fill the grid openings. The electroplating is continued until a cohesive layer of the second material with uniform height is created over the grating webs with this layer having a large absorption coefficient, the absorption properties of the grating structure of the grating are homogenized, so an improvement of the measurement signals that are generated with this grating is improved. Moreover, the mechanical stability of gratings produced in such a manner is improved.

12 Claims, 2 Drawing Sheets

X-RAY OPTICAL GRATING AND METHOD FOR THE PRODUCTION THEREOF, AND X-RAY DETECTOR EMBODYING SAME

BACKGROUND OF THE INVENTION

1. Field of the Invention

The present invention concerns a method to produce x-ray-optical gratings, x-ray-optical gratings and an x-ray system for x-ray dark field imaging and for x-ray phase contrast imaging.

2. Description of the Prior Art

It is known to produce an x-ray optical grating as follows. An x-ray-sensitive layer with an electrically conductive cover layer is applied on a base plate and a grating structure is transferred by a lithographic method into the x-ray-sensitive layer, so exposed and unexposed regions are created. The exposed regions of the x-ray-sensitive layer is dissolved so that a grating structure remains; a metal is introduced into the grating interstices by electroplating. A negative imprint of a grating made of metal remains after removing the x-ray-sensitive material and the base plate. A grating made of a first material is produced with this negative imprint, wherein this grating having a number of periodically arranged grating webs and grating openings, and the grating openings are filled by electroplating with a second material.

Such a method for the production of x-ray-optical gratings to generate x-ray dark field exposures and x-ray phase contrast exposures is known from DE 10 2006 037 281 A1. The term "x-ray-optical grating" as used herein means a grating that has certain absorption properties with regard to x-ray radiation.

Significant technological requirements for such an x-ray-optical grating exist with regard to the precision of the height of the absorbing structures thereof, the aspect ratio, and mechanical stability. Generally such gratings are produced according to a technique known as the LIGA method, from the German acronym for Röntgen-Lithographie, Galvanik, Abformung (x-ray lithography in English). In this procedure, a grating structure is first created in an x-ray-sensitive material via partial exposure with, for example, parallel synchrotron radiation, in which grating structure a metal is introduced by galvanic deposition. After the removal of the x-ray-sensitive material, this metal represents a negative with which a grating is produced from a material with low absorption coefficient. To improve the absorption properties of this grating, the grating openings are filled, by electroplating, with a different material that has a higher absorption coefficient.

In the x-ray-optical gratings produced according to the LIGA method, in particular in absorption gratings with a high aspect ratio, a number of parameters (for example the surface roughness, and what is known as the bath temperature) affect the deposition process of the second metal in the electroplating and lead to different growth heights within the grating gaps. The height of the filling between the individual grating webs can vary in some cases by up to 10-20%. These variances lead to a degradation of the measurement signal in x-ray dark field imaging and in x-ray phase contrast imaging, since the bands of generated high and low emission then deliver minima or maxima of different magnitudes that degrades the acquisition quality.

SUMMARY OF THE INVENTION

An object of the present invention is to provide a method for the production of x-ray-optical gratings for x-ray dark field imaging and for x-ray phase contrast imaging, and such an x-ray-optical grating itself that enable a uniform filling of the grating gaps of a grating with regard to the level of the filling, such that ultimately the quality of the measurement signal is maintained.

The invention is based on the insight that it is possible to design the process of electroplating to fill the grating gaps with a material with high absorption coefficient so that the grating structures are deliberately over-plated, so all grating gaps across the entire grating surface are filled with a highly absorbent material to their complete height, and additionally a cohesive and uniform layer of this filling material is created (most importantly with a uniform height) over (atop) the grating webs. It is furthermore advantageous that an improved mechanical stability of the gratings is achieved as a beneficial side-effect, due to the additional cohesion of the grating gaps filled in the electroplating process.

In accordance with the invention, the known method for the production of x-ray-optical gratings for x-ray dark field imaging and for x-ray phase contrast imaging is improved by an x-ray-sensitive layer with an electrically conductive cover layer being applied on a base plate, and a grating structure is transferred into the x-ray-sensitive layer by a lithographic method so exposed and unexposed regions are created, and the exposed regions of the x-ray-sensitive layer are dissolved so that a grating structure remains, and a metal is introduced into the grating interstices by electroplating, and after removing the x-ray-sensitive material and the base plate, a negative impression of a grating made of metal remains, and a grating made of a first material is produced with this negative impression, this grating having a number of periodically arranged grating webs and grating spacings (openings) and the grating gaps are filled with a second material by electroplating, with the electroplating being continued until a cohesive layer of the second material is created over the grating webs.

With regard to the absorption properties of the grating, it is advantageous for the x-ray absorption coefficient of the first material to be lower than the x-ray absorption coefficient of the second material. Different absorption coefficients in an x-ray-optical grating are a basic requirement for the function of such a grating since, upon irradiation of such a grating with x-ray radiation, differentiation should be made between radiation that has traversed the first material and radiation that has traversed the second material.

In an embodiment of the invention, the over-plated layer is produced to a uniform height, for example by polishing. Although, with regard to its absorption properties, the very thin layer can nearly be disregarded in comparison to the primary structures (grating webs and grating gaps), an exact, uniform, thickness-dependent absorption value results for the coated grating, whereby the absorption properties given a uniform height over the entire surface of the layer can be reproduced. This is particularly beneficial when many of these gratings (approximately 50 to 100) are mounted together on a CT detector and detect the measurement signals together. The layer thickness is thereby advantageously at least 5 μm, advantageously at least 10 μm.

An additional advantage of the layer is the increased mechanical strength the results therefrom. This is particularly advantageous if the gratings are used in a detector. In CT apparatuses of the 3rd generation with rotating detector, centrifugal forces between 20 and 40 g arise to which the gratings are exposed, and a strong mechanical stability is required.

The use of a plastic as a first material, advantageously polymethacrylate (PMMA) or an epoxy resin, has proven to be advantageous. These materials have a desired low x-ray absorption coefficient and are simple to handle in terms of their processing. Furthermore, epoxy resin in particular is very x-ray-insensitive.

Furthermore, it is advantageous to use a metal as a second material, advantageously gold or nickel. Metals are well suited for galvanic processing and possess a relatively high x-ray absorption coefficient. Good knowledge of the use of gold exists especially in microsystem production processes.

The described method is particularly suitable for gratings with a high aspect ratio. The aspect ratio is calculated from the ratio of the height of the grating to the period of the grating, wherein what is described with grating height is the height of the grating spacings and webs, and a period corresponds to the width of a grating web and a grating spacing together. It is primarily sought to achieve a high aspect ratio via an optimally large height of the grating, and this affects the absorption of the x-ray radiation traversing the grating since this is dependent on the layer thickness. For a given grating period, a high aspect ratio results in significant differences between the absorption maxima and minima so that after the grating the desired large differences arise in the intensity of the x-ray radiation exiting there.

The method according to the invention advantageously concerns x-ray-optical gratings that are constructed from two different materials, wherein the first material forms grating webs arranged in parallel which are connected at one end of the grating webs with one another via a flat substrate layer made from the first material, and grating spacings (openings) exist between the grating webs. Furthermore, the second material advantageously likewise forms grating webs which are arranged in the grating opening of the first material and are connected with one another by a cover layer made of the second material on the side of the grating facing away from the substrate layer. The arrangement of the grating webs advantageously ensues so that the grating webs of the second material are fit exactly into the grating openings of the first material, and the grating webs of the first material are fit exactly into the grating openings of the second material.

It is advantageous to produce the x-ray-optical grating according to the method described above, namely to attach an x-ray-sensitive layer with an electrically conductive cover layer on a base plate, afterward to transfer a grating structure into the x-ray-sensitive layer via a lithographic method, wherein exposed and unexposed regions are created and the exposed regions of the x-ray-sensitive layer are dissolved so that a grating structure remains. A metal can subsequently be introduced into the grating interstices via electroplating so that a negative impression of a grating made of metal remains after removal of the x-ray-sensitive material and the base plate, and a grating made from a first material can be produced with this negative impression.

In an advantageous embodiment of an x-ray system with a radiator/detector system for projective or tomographical x-ray dark field imaging and/or x-ray phase contrast imaging, at least one of the gratings used there is produced according to the method according to the invention.

DESCRIPTION OF THE PREFERRED EMBODIMENTS

Figure 1:
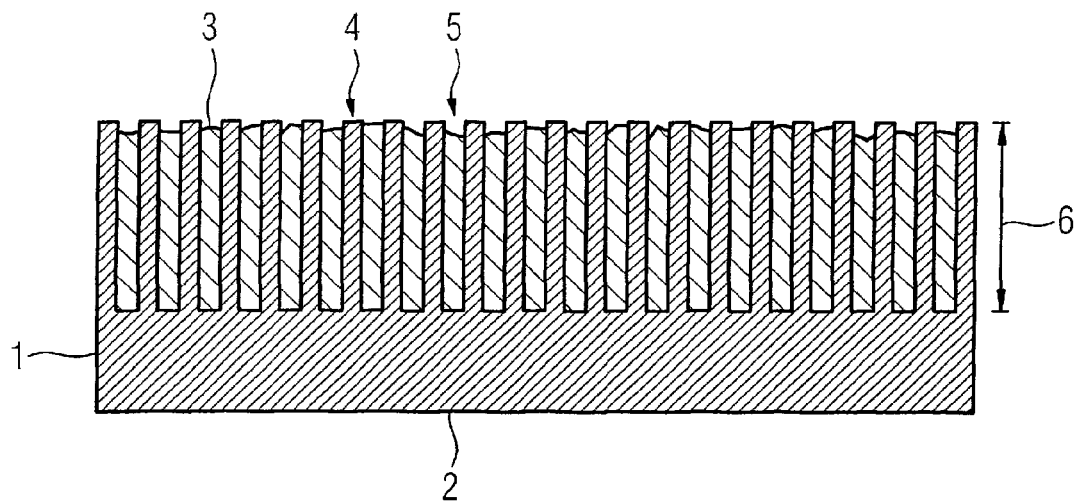
FIG. 1 shows a conventional grating with filling material in the grating openings.

FIG. 1 shows a conventional x-ray-optical grating 1 that was produced according to the LIGA method. An x-ray-sensitive layer—this is for the most part a plastic such as polymethacrylate, abbreviated as PMMA—is applied on a base plate. A grating structure is subsequently transferred via lithographic exposure with, for example, parallel synchrotron radiation. Exposed and unexposed regions are hereby created, wherein the exposed regions are subsequently dissolved. In the next step, a metal is filled into the grating openings (spacings) by electroplating. In an electrolytic bath, a voltage is thereby applied between the grating and an anode made of the metal to be plated. By electrolysis, metal ions detach from the anode and deposit by reduction on the cathode, to produce the grating. This is continued until a complete negative impression of a grating has been created. With the use of this negative impression, the grating 1 with periodically arranged grating webs 4 and grating gaps 5 is produced from a first material 2.

A second material 3 is visible in the grating gaps 5 of the grating gap 1. This material is likewise introduced via electroplating. Extremely small structures can be filled with a material via this technique. The deposition or accumulation of the metal ions thereby depends on multiple parameters, for example the bath temperature and the surface roughness of the grating material. In these known methods it is disadvantageous that the height of the electroplated material can thereby vary by 10% to 15% of the total height. These variances in the height of the second material 3 are also visible in the example shown here, meaning that the surface of the second material 3 in the grating gaps 5 does not always correspond to the height 6 of the surface of the grating 1. If such a grating is used as a source grating in a Talbot interferometer, corresponding differences in the absorption maxima and minima of the passing x-ray radiation that are formed by the grating also arise in a disadvantageous manner due to the different heights of the second material, so disadvantageous interference conditions (and therefore imprecise measurement signals) are generated.

Figure 2:
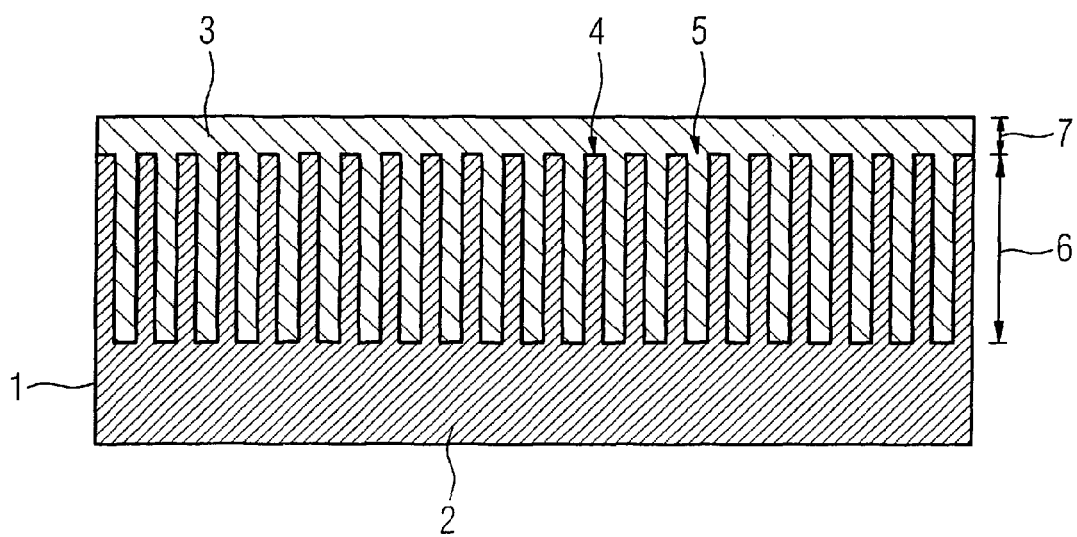
FIG. 2 shows a grating with a layer in accordance with the invention.

A grating 1 according to FIG. 1 with grating gaps 5 filled according to the invention is visible in FIG. 2, wherein a continuous layer of the filling material 3 is applied over the grating webs 4. For this purpose, the electroplating is conducted first until the grating gaps are filled and subsequently until the layer is created. In principle, a strong homogenization of the filling material is achieved solely via this overfilling of the grating gaps. According to the invention, this layer can additionally be brought to an additionally homogenized level 7 via polishing. The height 7 of the layer of the second material is thereby significantly smaller than the height 6 of the grating 1. The layer can thereby be disregarded in terms of its absorption properties. The low level 7 (which is uniform over the entire area of the grating 1) is advantageous if many gratings (for example approximately 50 to 100) are mounted together in a detector of a CT system.

With the described method, a height of the absorbing structures (advantageously gold structures) that is uniform over the entire grating area is achieved in the first place. The reproducibility of the absorption properties of the grating that is thus obtained is particularly helpful if many of these gratings (for example approximately 50-100) are mounted together on a CT detector and generate the measurement signals together. Furthermore, the mechanical strength of the grating is significantly increased. In the case of the installation of the grating in a CT gantry, the gratings are exposed to strong acceleration forces (approximately 20-40 g) during the acceleration of the CT gantry, which can lead to the destruction of the grating structures. The described over-plating leads to an increase of the mechanical stability of the grating webs, and thus of the entire grating composite.

Figure 3:
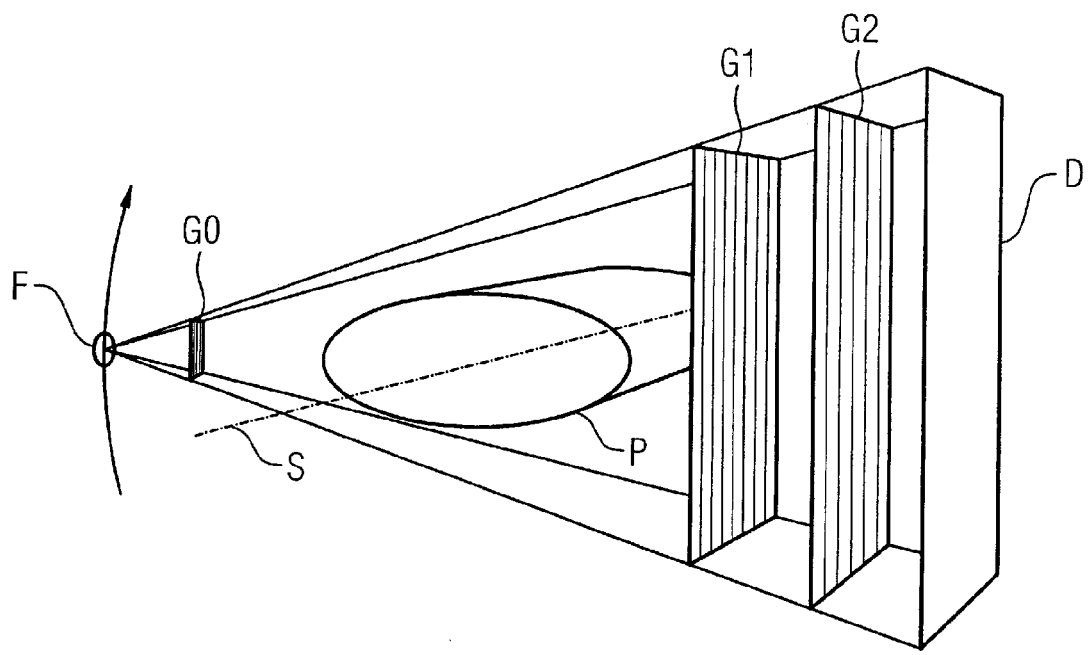
FIG. 3 shows a longitudinal section through a focus-detector system with depiction of absorption grating, phase grating and analysis grating and their grating structure.

FIG. 3 shows, as an example, an x-ray CT system with a radiator/detector system for projective or tomographical x-ray dark field imaging and/or x-ray phase contrast imaging a schematic 3D representation of a radiator/detector system of a CT apparatus. The gratings used here are of a source grating G0 to generate a bundle of quasi-coherent rays, the phase grating G1 to deflect the rays of the beam and generate interferences, and the analysis grating G2 directly before the detector D to determine phase shifts and scatter ratios. A sample P as an examination subject is arranged in the beam path. The focus F and the detector D are arranged on a gantry (not shown in detail here) and move in an orbit around the system axis S (represented as a dash-dot line). According to the invention, at least one of the gratings G0, G1 or G2 (advantageously at least the source grating G0 fashioned as an absorption grating) is produced according to the method described above. A predominantly homogeneous field of quasi-coherent radiation is hereby generated so that the interferences that are generated by the phase grating G1 can be optimally detected with measurement technology.

As a whole, an improvement of a method to produce x-ray-optical gratings, an x-ray-optical grating and an x-ray system is thus proposed with the invention, wherein these gratings consisting of a first material possess a plurality of periodically arranged grating webs and grating gaps, and the grating gaps are filled with a second material via electroplating. According to the invention, the electroplating is continued until a cohesive layer of the second material with uniform height is created over the grating webs. The absorption properties of the grating structure of the grating are homogenized via this layer with a large absorption coefficient, whereby an improvement of the measurement signal that is generated with this is produced. Moreover, the mechanical stability of gratings produced in this way is improved.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for producing x-ray-optical gratings for x-ray dark field imaging and for x-ray phase contrast imaging, comprising the steps of:
    applying an x-ray-sensitive layer with an electrically conductive cover layer on a base plate;
    transferring a grating structure into the x-ray-sensitive layer with a lithographic method, creating exposed and unexposed regions;
    dissolving the exposed regions of the x-ray-sensitive layer so that a grating structure remains;
    introducing a metal into the grating interstices by electroplating;
    removing the x-ray-sensitive material and the base plate so a negative impression of a grating made of metal remains;
    producing a grating made of a first material with this negative impression that has a plurality of periodically arranged grating webs and grating openings; and
    filling the grating openings with a second material by electroplating, by continuing the electroplating until a cohesive layer of the second material is created over the grating webs.

2. A method as claimed in claim 1, comprising employing a first material having an x-ray absorption coefficient that is lower than the x-ray absorption coefficient of the second material.

3. A method as claimed in claim 1 comprising producing the layer of the second material to a uniform height by polishing.

4. A method as claimed in claim 1 comprising implementing the electroplating to give the second material a layer thickness of at least 5 μm.

5. A method as claimed in claim 1 comprising implementing the electroplating to give the second material a layer thickness of at least 10 μm.

6. A method as claimed in claim 1 comprising employing a plastic as a first material.

7. A method as claimed in claim 6 comprising employing a polymethacrylate as the first material.

8. A method as claimed in claim 1 comprising employing an epoxy resin as the first material.

9. A method as claimed in claim 1 comprising employing a metal as the second material.

10. A method as claimed in claim 9 comprising employing gold as the second material.

11. A method as claimed in claim 9 comprising employing nickel as the second material.

12. A method as claimed in claim 1 comprising producing the grating with an aspect ratio of at least 50.

* * * * *